United States Patent
Ein-Gal

(10) Patent No.: US 7,576,344 B2
(45) Date of Patent: Aug. 18, 2009

(54) TARGET POSITIONER

(76) Inventor: Moshe Ein-Gal, 30 Azar Street, Ramat Hasharon 47203 (IL)

( * ) Notice: Subject to any disclaimer, the term of this patent is extended or adjusted under 35 U.S.C. 154(b) by 284 days.

(21) Appl. No.: 11/757,372

(22) Filed: Jun. 3, 2007

(65) Prior Publication Data
US 2008/0298536 A1 Dec. 4, 2008

(51) Int. Cl.
*A61B 6/08* (2006.01)
*A61N 5/10* (2006.01)

(52) U.S. Cl. ........... 250/505.1; 250/451; 250/492.1; 378/68; 378/197; 378/204; 378/205; 600/427; 600/436; 606/1; 606/130

(58) Field of Classification Search .......... None
See application file for complete search history.

(56) References Cited

U.S. PATENT DOCUMENTS

| | | | |
|---|---|---|---|
| 2,798,958 A * | 7/1957 | Hudson et al. ............. 378/39 |
| 3,506,826 A * | 4/1970 | Kosters .................... 5/601 |
| 3,848,132 A * | 11/1974 | Foderaro ................. 378/209 |
| 4,019,059 A * | 4/1977 | Brundin et al. ............ 378/209 |
| 4,174,481 A * | 11/1979 | Liebetruth ................ 378/20 |
| 4,291,229 A * | 9/1981 | Patt ...................... 378/180 |
| 4,477,922 A * | 10/1984 | Liebetruth ................ 378/20 |
| 4,566,444 A * | 1/1986 | Spolyar .................. 606/130 |
| 4,583,537 A * | 4/1986 | Derechinsky et al. ....... 606/130 |
| 4,645,933 A * | 2/1987 | Gambini et al. ......... 250/363.05 |
| 4,885,998 A * | 12/1989 | Span et al. ............... 108/139 |
| 4,912,754 A * | 3/1990 | Van Steenburg ........... 378/209 |
| 4,974,243 A * | 11/1990 | McArdle et al. ............ 378/38 |
| 5,148,454 A * | 9/1992 | Coffman .................. 378/40 |
| 5,189,687 A * | 2/1993 | Bova et al. ............... 378/65 |
| 5,879,281 A * | 3/1999 | Ein-Gal .................. 600/1 |
| 5,957,933 A * | 9/1999 | Yanof et al. .............. 606/130 |
| 6,212,251 B1 * | 4/2001 | Tomura et al. ............. 378/15 |
| 6,246,900 B1 * | 6/2001 | Cosman et al. ............ 600/426 |
| 6,249,695 B1 * | 6/2001 | Damadian ................ 600/427 |
| 6,256,528 B1 * | 7/2001 | Zonneveld et al. ......... 600/425 |
| 6,275,564 B1 * | 8/2001 | Ein-Gal ................... 378/68 |
| 6,565,577 B2 * | 5/2003 | Cosman .................. 606/130 |
| 6,636,622 B2 * | 10/2003 | Mackie et al. ............. 382/132 |
| 6,725,084 B2 * | 4/2004 | Stark .................... 600/436 |

(Continued)

Primary Examiner—David A. Vanore
(74) Attorney, Agent, or Firm—Dekel Patent Ltd; David Klein

(57) ABSTRACT

A target positioner including a radiation source disposed in a source housing, the radiation source adapted to emit a radiation beam, a target holder adapted to be attached to and generally immobilize a target organ, the target holder being rotatingly attached to a bearing assembly, a patient support table for supporting a patient thereon, a rotator for turning the patient support table about a rotation axis, and a source arm fixedly attached at one portion thereof to the source housing and at another portion thereof to the bearing assembly, such that when the target holder is attached to a target organ and the rotator turns the patient support table about the rotation axis, the target holder constrains the target organ from translating with respect to the radiation source and the source housing, and wherein the target holder permits the target organ to rotate by means of the bearing assembly relative to the source housing while experiencing slight translations with respect to the patient support table, so that the radiation beam emanating from the radiation source impinges upon the target organ at a plurality of angles irrespective of the misalignments between the radiation beam and the patient support table and between the patient support table and the target organ.

12 Claims, 2 Drawing Sheets

U.S. PATENT DOCUMENTS

| | | | |
|---|---|---|---|
| 6,848,826 B2* | 2/2005 | Marie et al. | 378/196 |
| 7,011,447 B2* | 3/2006 | Moyers | 378/204 |
| 7,014,361 B1* | 3/2006 | Ein-Gal | 378/197 |
| 7,298,821 B2* | 11/2007 | Ein-Gal | 378/68 |
| 7,404,674 B2* | 7/2008 | Eichenseer | 378/209 |
| 7,492,858 B2* | 2/2009 | Partain et al. | 378/37 |
| 7,496,398 B2* | 2/2009 | Nields et al. | 600/427 |
| 2003/0152197 A1* | 8/2003 | Moyers | 378/204 |
| 2004/0030241 A1* | 2/2004 | Green et al. | 600/422 |
| 2004/0184578 A1* | 9/2004 | Nakano | 378/65 |
| 2004/0254566 A1* | 12/2004 | Plicchi et al. | 606/1 |
| 2005/0187424 A1* | 8/2005 | Hambuchen et al. | 600/12 |
| 2006/0036160 A1* | 2/2006 | Altman et al. | 600/415 |
| 2008/0240353 A1* | 10/2008 | Myles | 378/65 |
| 2008/0298536 A1* | 12/2008 | Ein-Gal | 378/4 |
| 2009/0049613 A1* | 2/2009 | Dippl et al. | 5/611 |

* cited by examiner

TARGET POSITIONER

FIELD OF THE INVENTION

The present invention relates generally to irradiation systems for delivering radiation beams to a target, and more particularly to a target positioner that constrains a target organ to be precisely positioned with respect to a radiation source.

BACKGROUND OF THE INVENTION

Irradiating a target, such as in radiation treatment, requires a multiplicity of orientations between a target to be irradiated and a radiation beam. Typically, a radiation source is mounted on a gantry that rotates about a horizontal gantry axis. The radiation beam intersects, and is generally perpendicular to, the gantry axis. A patient is supported by a turntable that rotates the target about a vertical target axis, which theoretically intersects the gantry axis. Linear accelerators and cobalt therapy devices incorporate such gantry and turntable rotations to accomplish multi-orientation irradiation.

Since the beam is positioned by the gantry while the target is independently positioned by the table, the rotation axes of the gantry and turntable do not perfectly intersect with the radiation beam at the theoretical intersection point (isocenter). Rather, in the real world, there is a slight misalignment between the three, among other things due to the size and weight of the sagging rotating gantry and turntable. Consequently, an undesirable displacement or misalignment of the radiation beam occurs relative to the turntable.

Additional beam/target displacement may occur during treatment by target motion relative to the turntable, e.g., due to breathing. Patient support means in the prior art attempt to immobilize the patient's body relative to the turntable, but no such immobilization is described in the prior art for internal organ displacements relative to the immobilized body. Prior art methods, therefore, suffer from imprecise positional relationships between the table and the source compounded by uncontrolled target motion relative to the table. Beam/target displacements may be statically and dynamically compensated by on-line measurements and repositioning the target and/or the beam in a costly process known as Image Guided Radiation Therapy (IGRT).

SUMMARY OF THE INVENTION

The present invention seeks to provide a novel target positioner that constrains a target organ to be precisely positioned with respect to a radiation source, as is described in more detail hereinbelow.

There is thus provided in accordance with an embodiment of the present invention a target positioner including a radiation source disposed in a source housing, the radiation source adapted to emit a radiation beam, a target holder adapted to be attached to and generally immobilize a target organ, the target holder being rotatingly attached to a bearing assembly, a patient support table for supporting a patient thereon, a rotator for turning the patient support table about a rotation axis, and a source arm fixedly attached at one portion thereof to the source housing and at another portion thereof to the bearing assembly, such that when the target holder is attached to a target organ and the rotator turns the patient support table about the rotation axis, the target holder constrains the target organ from translating with respect to the radiation source and the source housing, and wherein the target holder permits the target organ to rotate by means of the bearing assembly relative to the source housing while experiencing slight translations with respect to the patient support table, so that the radiation beam emanating from the radiation source impinges upon the target organ at a plurality of angles irrespective of the misalignments between the radiation beam and the patient support table and between the patient support table and the target organ.

In accordance with a non-limiting embodiment of the present invention, the target positioner further includes a safety controller operable to limit displacement between the target holder and the patient support table to a pre-determined level. The safety controller may include at least one sensor for sensing movement of the target holder with respect to the patient support table. The safety controller may include an actuator for moving the patient support table to correct for any misalignment sensed by the at least one sensor. The safety controller may also operate the rotator to correct for any misalignment sensed by the at least one sensor. The safety controller may be programmed to stop motion of the patient support table and irradiation of the radiation source towards the target organ in the event of an emergency or malfunction, for example, when a displacement between the target holder and the patient support exceeds a predetermined level.

In accordance with another non-limiting embodiment of the present invention, the bearing assembly includes a single bearing. Alternatively, the bearing assembly includes a first bearing and a second bearing attached to different portions of a link member, the first bearing permitting rotation about a different rotation axis than a rotation axis of the second bearing. The radiation source may be rotatable about a rotation axis. In such an embodiment, the rotation axes of the first and second bearing may be generally collinear with rotation axes of the patient support table and the radiation source.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1:
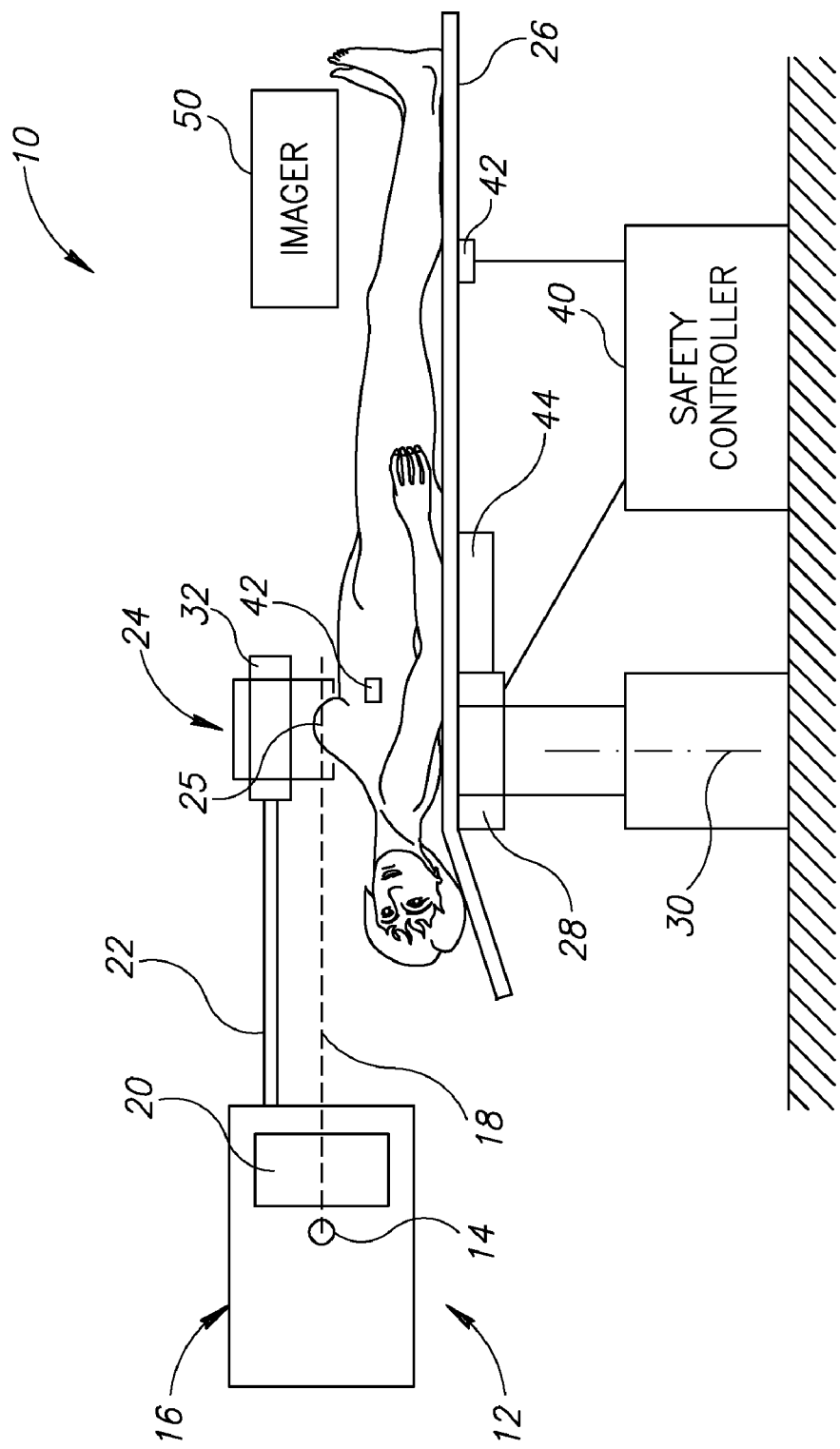
FIG. 1 is a simplified pictorial illustration of a target positioner, constructed and operative in accordance with an embodiment of the present invention.

Reference is now made to FIG. 1, which illustrates a target positioner 10 for use with a radiation system 12, constructed and operative in accordance with an embodiment of the present invention.

The radiation system 12 includes a radiation source 14 disposed in a stationary source housing 16. Radiation source 14 may be any source suitable that emits a radiation beam 18 for performing irradiation, such as but not limited to, X-ray beams (e.g., at MV energy spectrum or other levels of energy), beta ray beams, positron beams, proton beams, antiproton beams, neutron beams, heavy ion beams, e.g., alpha ray beams, carbon ion beams, etc. Radiation beam 18 may be collimated by a collimator 20, such as but not limited to, a multiple layer multileaf collimator, such as that described in U.S. Pat. Nos. 6,266,393 and 6,526,123 to Ein-Gal, the disclosures of which are incorporated herein by reference.

Target positioner 10 achieves beam/target positioning by means of a source arm 22 that is fixedly attached at one portion thereof to source housing 16 and at another portion thereof to a bearing assembly 32. A target holder 24 is rotatingly attached to bearing assembly 32. Target holder 24 is adapted to be attached to a target organ 25 such as but not limited to, a breast or skull (for example, by means of vacuum, adhesive, fasteners and others and any combination thereof). Source arm 22 and target holder 24 may be made of rigid, medically safe materials, such as but not limited to, stainless steel (e.g., AISI 316L) or titanium alloy.

In a preferred embodiment, a patient support table 26 (also referred to as a turntable or simply patient support) is provided for supporting a patient thereon. A rotator 28 is provided for turning patient support table 26, such as about a (e.g., vertical) rotation axis 30 (rotation in azimuth). In the embodiment of FIG. 1, bearing assembly 32 comprises a single bearing (e.g., a ball bearing ring), such that the patient can be rotated about axis 30. The target holder 24 constrains the target organ 25 from translating with respect to axis 30 and the combination of the target holder 24 and the source arm 22 prevents the target organ 25 from moving with respect to source 14 and stationary source housing 16. However, target holder 24 does permit the target organ 25 to rotate together with the table 26 about axis 30. In this manner, the radiation beam 18 emanating from the radiation source 14 can impinge upon the target organ 25 at a plurality of angles (e.g., full 360° movement).

Theoretically the radiation beam 18 intersects rotation axis 30 throughout the azimuthal movement. However, since the target position is determined by that of the source 14 and not the table 26 (due to the source arm 22), in real life minute target-to-table displacements may take place. Accordingly, minute displacements may take place between the target organ 25 and the patient's body supported by table 26. In accordance with an embodiment of the present invention, a safety controller 40 is provided operable to limit the magnitude of any displacement between the target holder 24 and table 26 to a pre-determined level. The safety controller 40 may include one or more sensors 42 (e.g., accelerometers that sense movement of the body or table, or optical sensors that sense movement of fiducial markers on the body or table) for sensing movement of the patient and/or target holder 24 with respect to table 26, and an actuator 44 (e.g., step motor, linear actuator, etc.) for moving the table 26 to correct for any misalignment sensed by the sensors 42. The safety controller 40 can also operate rotator 28 to correct for any misalignment sensed by the sensors 42. The safety controller 40 can limit such target/body displacements to a pre-determined level in order to alleviate risks associated with large target-to-body displacements. In accordance with another embodiment, the safety controller 40 may also be equipped to stop all motion and irradiation if necessary.

Imaging apparatus 50 may also be provided for imaging the target organ 25 during treatment. Techniques suitable for imaging target organ 25 with imaging apparatus 50 include, but are not limited to, planar radiography, ultrasound, computed tomography (CT), single photon emission computed tomography (SPECT), magnetic resonance imaging (MRI), magnetic resonance spectroscopy (MRS), positron emission tomography (PET), thermal imaging and others. Imaging apparatus 50 may include an imaging detector arm rigidly attachable to the source arm 22 and which supports an imaging detector. The imaging detector detects radiation beam 18 and produces an image of target organ 25, and may also determine target shape.

Figure 2:
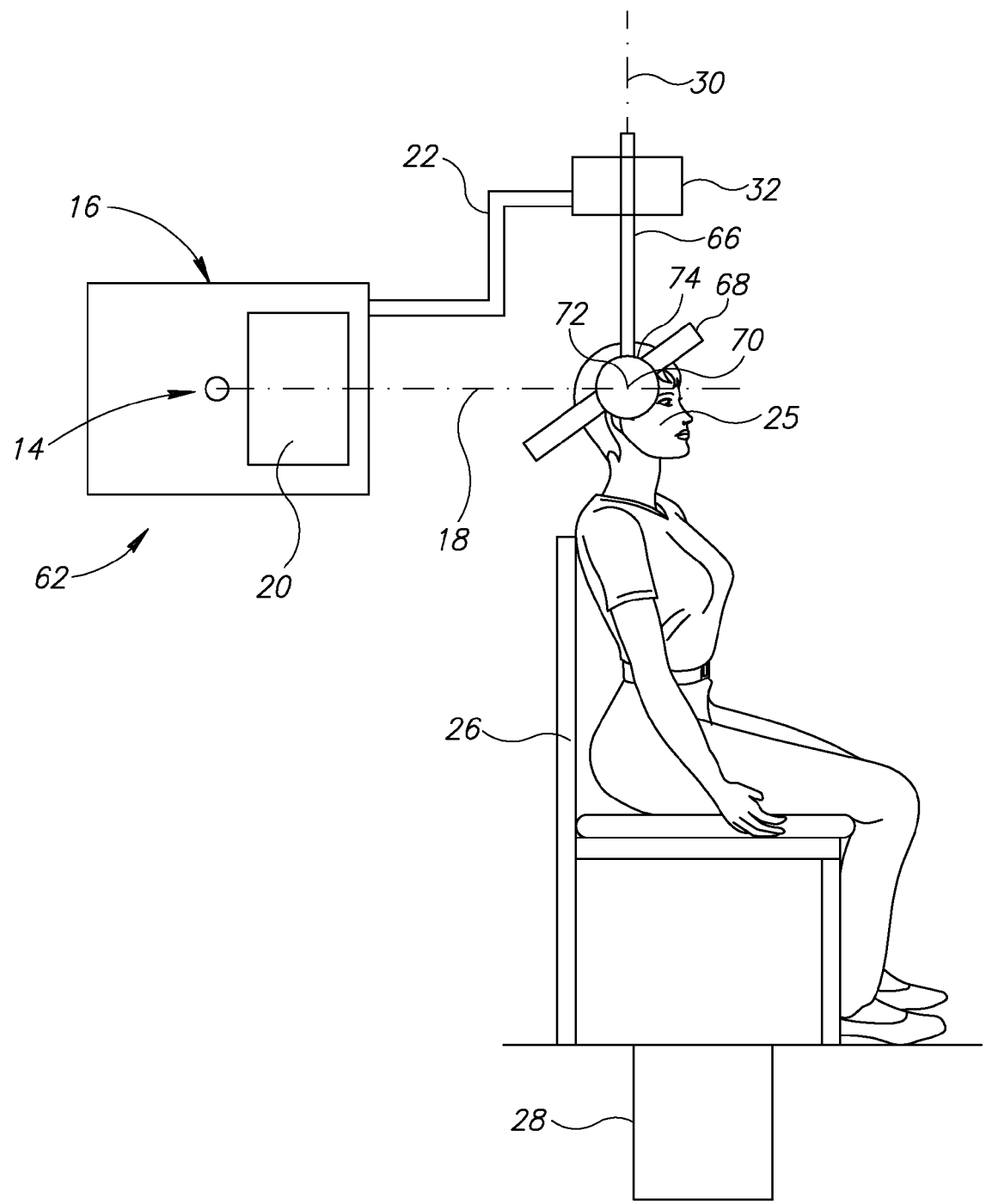
FIG. 2 is a simplified pictorial illustration of another target positioner, constructed and operative in accordance with another embodiment of the present invention.

Reference is now made to FIG. 2, which illustrates a target positioner 60 for use with a radiation system 62, constructed and operative in accordance with an embodiment of the present invention.

Target positioner 60 and radiation system 62 are similar to target positioner 10 and radiation system 12, with like elements being designated by like numerals. Target positioner 60 differs from target positioner 10 by using a target holder 68 and a bearing assembly that has two bearings: a first bearing 32 and a second bearing 70 attached to different portions of a link member 66. Link member 66 is rigid in the illustrated embodiment. The source arm 22 is rotatingly attached to first bearing 32, and the target holder 68 is rotatingly attached to second bearing 70. The target holder 68 is secured to the target organ 25 (e.g., the skull). As with target positioner 10, the patient can be rotated about axis 30. In addition, in this embodiment, the patient can be rotated about a second axis 72 (pitch axis, which is perpendicular into the drawing sheet and intersects axis 30). The target holder 68 constrains the target organ 25 from translating with respect to axis 30 and axis 72 and the combination of the target holder 68 and the source arm 22 prevents the target organ 25 from moving with respect to source 14 and stationary source housing 16. However, target holder 68 does permit the target organ 25 to rotate together with the table 26 (the "table" in the illustrated embodiment being a chair; the term "table" will be used interchangeably with chair throughout the specification and claims) about axis 30 and allows for rotation about axis 72. In this manner, the radiation beam 18 emanating from the radiation source 14 can impinge upon the target organ 25 at a plurality of angles (e.g., movement in azimuth and pitch). Target positioner 60 may employ the same or similar safety controller 40 and imaging apparatus 50, not shown for simplicity. For example, safety controller 40 may operate a pitch rotator 74 that provides adjustments about axis 72.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A target positioner comprising:

a radiation source disposed in a source housing, said radiation source adapted to emit a radiation beam;

a target holder adapted to be attached to and generally immobilize a target organ, said target holder being rotatingly attached to a bearing assembly;

a patient support table for supporting a patient thereon;

a rotator for turning said patient support table about a rotation axis; and a source arm fixedly attached at one portion thereof to said source housing and at another portion thereof to said bearing assembly, such that when said target holder is attached to a target organ and said rotator turns said patient support table about said rotation axis, said target holder constrains said target organ from translating with respect to said radiation source and said source housing, and wherein said target holder permits said target organ to rotate by means of said bearing assembly relative to said source housing while experiencing slight translations with respect to said patient support table, so that said radiation beam emanating from said radiation source impinges upon said target organ at a plurality of angles irrespective of said misalignments between said radiation beam and said patient support table and between said patient support table and said target organ.

2. The target positioner according to claim 1, further comprising a safety controller operable to limit displacement between said target holder and said patient support table to a pre-determined level.

3. The target positioner according to claim 2, wherein said safety controller comprises at least one sensor for sensing movement of said target holder with respect to said patient support table.

4. The target positioner according to claim 3, wherein said safety controller comprises an actuator for moving said patient support table to correct for any misalignment sensed by said at least one sensor.

5. The target positioner according to claim 2, wherein said safety controller operates said rotator to correct for any misalignment sensed by said at least one sensor.

6. The target positioner according to claim 2, wherein said safety controller is operative to stop motion of said patient support table and irradiation of said radiation source towards the target organ.

7. The target positioner according to claim 1, further comprising imaging apparatus for imaging the target organ.

8. The target positioner according to claim 1, wherein said target holder comprises a breast holder operable to immobilize a breast by means of vacuum.

9. The target positioner according to claim 1, wherein said target holder comprises a holder for immobilizing a patient's skull.

10. The target positioner according to claim 1, wherein said bearing assembly comprises a single bearing.

11. The target positioner according to claim 1, wherein said bearing assembly comprises a first bearing and a second bearing attached to different portions of a link member, said first bearing permitting rotation about a different rotation axis than a rotation axis of said second bearing.

12. The target positioner according to claim 11, wherein said radiation source is rotatable about a rotation axis and wherein said rotation axes of said first and second bearing are generally collinear with rotation axes of said patient support table and said radiation source.

* * * * *